United States Patent [19]

Erbil

[11] Patent Number: 4,992,305

[45] Date of Patent: Feb. 12, 1991

[54] CHEMICAL VAPOR DEPOSITION OF TRANSISTION METALS

[75] Inventor: Ahmet Erbil, Atlanta, Ga.

[73] Assignee: Georgia Tech Research Corporation, Atlanta, Ga.

[21] Appl. No.: 210,079

[22] Filed: Jun. 22, 1988

[51] Int. Cl.⁵ .................... C23C 16/00; C07F 11/00; C07F 17/00
[52] U.S. Cl. .................. 427/252; 427/226; 427/229; 427/255.3; 427/314; 556/1; 556/43; 556/58; 556/136; 556/140
[58] Field of Search .............. 427/229, 226, 252, 314; 255.3; 556/1, 43, 46, 136, 140, 58

[56] References Cited

U.S. PATENT DOCUMENTS

| | | | |
|---|---|---|---|
| 2,818,416 | 12/1957 | Brown et al. | 260/429 |
| 2,839,552 | 6/1958 | Shapiro et al. | 260/429 |
| 2,864,843 | 12/1958 | DeWitt et al. | 260/429.9 |
| 2,898,235 | 8/1959 | Bulloff | 117/107 |
| 2,911,424 | 11/1959 | Kaufman | 260/429.3 |
| 2,916,503 | 12/1959 | Kozikowski | 260/429 |
| 2,917,501 | 12/1959 | Drucker et al. | 260/94.9 |
| 2,920,090 | 1/1960 | Lindstrom et al. | 260/429 |
| 2,921,948 | 1/1960 | Brantley | 260/429 |
| 2,969,382 | 1/1961 | Mangham | 260/448 |
| 2,971,017 | 2/1961 | Fischer et al. | 260/429 |
| 2,976,304 | 3/1961 | DeWitt et al. | 260/429 |
| 2,977,381 | 3/1961 | Roha et al. | 260/448 |
| 2,987,531 | 6/1961 | Shapiro et al. | 260/429 |
| 3,018,194 | 1/1962 | Norman et al. | 117/107 |
| 3,028,406 | 4/1962 | Brantley | 260/439 |
| 3,030,393 | 4/1962 | Bulloff | 260/429 |
| 3,032,569 | 5/1962 | Freeman et al. | 260/429 |
| 3,038,915 | 6/1962 | Barkdoll et al. | 260/429.5 |
| 3,061,464 | 10/1962 | Norman et al. | 117/107 |
| 3,061,465 | 10/1962 | Norman et al. | 117/107 |
| 3,064,020 | 11/1962 | Riemschneider | 260/429 |
| 3,071,493 | 1/1963 | Whaley et al. | 117/107 |
| 3,071,605 | 1/1963 | Morehouse | 260/429 |
| 3,080,305 | 3/1963 | Gorsch | 204/158 |
| 3,089,886 | 5/1963 | Breederueld et al. | 260/H29.5 |
| 3,099,689 | 7/1963 | Cragg | 260/561 |
| 3,114,652 | 12/1963 | Schetky | 117/93.1 |
| 3,144,472 | 8/1964 | Werner et al. | 556/43 |
| 3,152,157 | 10/1964 | Shapiro et al. | 260/438 |
| 3,175,924 | 3/1965 | Norman et al. | 117/107.2 |
| 3,188,230 | 6/1965 | Bakish et al. | 117/107.2 |
| 3,253,946 | 5/1966 | Kozikowski et al. | 117/107.2 |
| 3,259,642 | 7/1966 | Schenck et al. | 260/429 |
| 3,288,829 | 11/1966 | Wilkinson | 260/429 |
| 3,294,654 | 12/1966 | Norman et al. | 204/38 |
| 3,328,440 | 6/1967 | Shapiro et al. | 260/429 |
| 3,426,052 | 2/1969 | Hubel et al. | 260/429 |
| 3,673,232 | 6/1972 | Talbot et al. | 260/439 |
| 3,914,515 | 10/1975 | Kane | 428/432 |
| 4,359,490 | 11/1982 | Lehrer | 427/95 |
| 4,496,610 | 1/1985 | Cattell et al. | 427/66 |
| 4,720,560 | 1/1988 | Hui et al. | 556/1 |

OTHER PUBLICATIONS

Dapkus, P. D., *Ann. Rev. Mater. Sci.*, 1982, vol. 12, pp. 243-269.
Green, M. L. & Levy, R. A., *Journal of Metals*, Jun. 1985, pp. 67-71.
Tsang, W. T., *Appl. Phys. Lett.*, 1984, vol. 45, pp. 1234-1236.
Wilkinson, G., et al., *J. Inorganic & Nuclear Chemistry*, vol. 2, 1956, pp. 32-37.

*Primary Examiner*—Janyce Bell
*Attorney, Agent, or Firm*—Oldham & Oldham Co.

[57] ABSTRACT

Coatings of Group IIA metals and compounds thereof are formed by chemical vapor deposition, in which a heat decomposable organometallic compound of the formula (I)

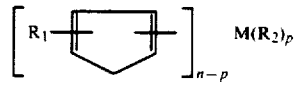

wherein M is a transition metal of Group VB, VIB, VIIB or VIII, $R_1$ is a lower alkyl or alkenyl radical containing from 2 to about 6 carbon atoms, $R_2$ is a hydrogen or lower alkyl or alkenyl radical, n is the valence of M and is an integer from 2 to 4, and p is an integer from 0 to $(n-1)$, is contacted with a heated substrate which is above the decomposition temperature of the organometallic compound. The pure metal is obtained when the compound of the formula I is the sole heat decomposable compound present and deposition is carried out under nonoxidizing conditions. Intermetallic compounds such as manganese telluride can be deposited from a manganese compound of formula I and a heat decomposable tellurium compound under nonoxidizing conditions.

17 Claims, No Drawings

CHEMICAL VAPOR DEPOSITION OF TRANSISTION METALS

TECHNICAL FIELD

This invention relates to processes for forming a thin metallic coating on a heated substrate by decomposition of a thermally decomposable organometallic compound, and to thermally decomposable organometallic compounds used in such processes.

BACKGROUND ART

Chemical vapor deposition has been extensively described in the literature (including patents) as a technique for depositing a thin metallic coating on a heated substrate. Basically, a heat decomposable volatile metal compound (usually an organometallic compound), which may be called the precursor, is contacted with a substrate which has been heated to a temperature above the decomposition temperature of the metal compound. The metallic coating may be a metal, metal mixture or alloy, or metal compound or mixture thereof, depending on the choice of precursor(s) and reaction conditions.

While the technique has been described with reference to most transition metals and to certain other metals and metalloids (silicon, for example), commercial use of CVD for the most part has been confined to deposition of a few metals and metal compounds, such as silicon, tungsten, and certain III-V and II-VI compounds (denoting, respectively, a compound of a Group III metal and a Group V element, and a compound of a Group II metal and a Group VI element). The absence of suitable heat decomposable organometallic compounds for elements other than those mentioned above appears to have limited the extension of CVD to the deposition of other metals or compounds.

DISCLOSURE OF THE INVENTION

According to one aspect of this invention, a metallic coating is formed on a heated substrate by contacting a heat decomposable organometallic compound having the formula (I)

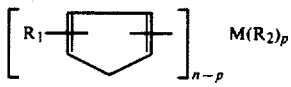

wherein:

M is a metal of Group VB, VIB, VIIB or VIII of the Periodic Table;

$R_1$ is a lower alkyl radical of 2 to 6 carbon atoms;

$R_2$ is hydrogen or a lower alkyl radical of 1 to about 6 carbon atoms, or a lower alkenyl radical of 2 to about 6 carbon atoms;

n is the valence of M and is an integer from 2 to 4; and p is an integer from 0 to $(n-1)$; the temperature of said substrate being above the decomposition temperature of said organometallic compound.

The term, "hydrocarbyl" is used for convenience herein to denote the carbon-containing radicals specifically named in the definition of $R_2$ above. This term shall not be construed herein as including any other radicals.

In the above formulas and accompanying definitions, "Group VIII metal" is preferably iron, cobalt, nickel, ruthenium, rhodium, palladium, osmium, iridium or platinum.

Best results are obtained when organometallic precursor compounds of the formula (I) are selected in accordance with the following provisos:

(1) M is a metal of Group VB, VIB, or VIII when $p=0$;

(2) M is a metal of Group VB, VIB or VIIB when $R_2$ is hydrogen; and (3) M is a Group VIII metal when $R_2$ is a hydrocarbyl radical.

This invention according to another aspect provides novel organometallic precursor compounds of the above formula (I) in which M, $R_1$, $R_2$, n and p are as previously defined with the provisos that:

(1) M is a metal of Group VB when $p=0$;

(2) M is a metal of Group VIB or VIIB when $R_2$ is hydrogen and p is from 1 to $(n-1)$; and (3) M is a metal of Group VIIB or VIII when $R_2$ is a hydrocarbyl radical of 1 about 6 carbon atoms, and p is from 1 to $(n-1)$.

In other words, the novel organometallic precursor compounds of formula (I) are: (a) Group VB metal compounds in which $p=0$; (b) Group VIB metal compounds in which $R_2$ is hydrogen and p is from 1 to $(n-1)$; (c) Group VIIB metal compounds in which $R_2$ is hydrogen or a hydrocarbyl radical and p is from 1 to $(n-1)$; and (d) Group VIII metal compounds in which $R_2$ is a hydrocarbyl radical and p is from 1 to $(n-1)$.

The groups of the Periodic Table herein are according to the usage of "The Condensed Chemical Dictionary", 10th edition, 1981, page 789, revised by G. G. Hawley, published by Van Nostrand Reinhold Company, New York.

Subject to the provisos where indicated, the definitions of M, $R_1$, $R_2$, n and p are uniform throughout the specification and claims.

BEST MODE FOR CARRYING OUT THE INVENTION

The heat decomposable organometallic compounds which are used as precursors in the practice of this invention meet the following requirements: (1) they are liquids at 100° C., (i.e. the melting points are below 100° C.); (2) they have vapor pressures of at least 0.1 torr at 100° C.; (3) they clearly decompose to deposit metal with little or no carbon incorporation (i.e., not more than about 5 percent by weight of carbon in the metal); (4) they are thermally stable at temperatures below about 150° C.; and (5) they thermally decompose with the deposition of metal at a temperature from about 150° C. to about 1000° C.

The low melting points and the large temperature difference between the melting point and the decomposition temperature of precursor compounds used herein make it possible to disperse the liquid precursors into a carrier gas stream at convenient operating temperatures without risk of premature decomposition. High vapor pressure at 100° C., assures a sufficiently high concentration of precursor in carrier gas for effective metal oxide deposition. The thermal decomposition temperatures of the precursors are low enough for economical operation, with few if any requirements for special high temperature resistant equipment in most cases. Finally, precursors herein give highly pure deposits under suitable deposition conditions.

The precursors used herein meet the above requirements and generally have lower melting points and higher vapor pressures at 100° C., and usually have greater temperature differences between the melting point and the decomposition temperature than their cyclopentadienyl metal analogs in which the cyclopentadienyl radical is unsubstituted.

Precursors for depositing transition metals of Group VB, VIB, VIIB, or VIII in accordance with this invention are compounds of formula (I) as aforedescribed.

Preferred organometallic precursor compounds for depositing transition metals of Group IIA metal oxides and Group VB to Group VIII metals are as follows:

(1) Metal alkylcyclopentadienyls of formula (I) in which $p=0$, $R_2$ is absent, and M is a metal of Group VB, VIB, or VIII.

(2) Alkylcyclopentadienyl metal hydrides of formula (I) in which $R_2=H$ and M is a metal of Group VB, VIB, or VIIB.

(3) Alkylcyclopentadienyl metal compounds in which $R_2$ is a hydrocarbyl radical of 1 to about 6 carbon atoms, i.e., an alkyl ($C_1$–$C_6$), or alkenyl ($C_2$–$C_6$) radical, and M is a Group VIII metal.

The above preferred precursor compounds are indicated in tabular form in TABLE I below, in which the columns give the various possible values of $R_2$ and the rows give the groups of the Periodic Table which are included within the definition of $M_1$. An "x" at the intersection of a given row and column denotes a preferred group of compounds.

TABLE 1

| | Preferred CVD Precursors of Formula I | | |
|---|---|---|---|
| Metal Group | $R_2$ is Absent | $R_2$ = H | $R_2$ = HC* |
| VB | x | x | |
| VIB | x | x | |
| VIIB | | x | x |
| VIII | x | | x |

*HC in TABLE 1 denotes alkyl of 1 to about 6 carbon atoms or alkenyl of 2 to about 6 carbon atoms.

Metals which can be deposited according to this invention are transition metals, i.e., metals of Groups VB, VIB, VIIB, VIII. The term "transition metal", as used herein is as defined in the Condensed Chemical Dictionary, 10th edition, 1981, page 1036, revised by G. G. Hawley; published by Van Nostrand Reinhold Company, New York. By way of example, without limitation thereto, metals which can be deposited in accordance with this invention include vanadium, niobium and tantalum (Group VB); chromium, molybdenum and tungsten (wolfram) (Group VIB); manganese and rhenium (Group VIIB); and iron, cobalt, nickel, ruthenium, rhenium, palladium, osmium, iridium and platinum (Group VIII). Preferred Group VIII metals are iron, cobalt, nickel, ruthenium, rhodium, palladium, osmium and iridium, especially iron, cobalt and nickel. The symbol M in formula (I) denotes the metal to be deposited.

The aliphatic substituent $R_1$ on the cyclopentadienyl ring contains from 2 to about 6 carbon atoms, preferably 2 to about 4 carbon atoms, and may be either alkyl or alkenyl. Suitable alkyl substituents include ethyl, propyl, isopropyl, butyl, isobutyl, sec-butyl, pentyl and hexyl. Suitable alkenyl substituents include vinyl, allyl, isopropenyl, 1-butenyl, 2-butenyl and 3-butenyl. The alkyl substituents are preferred. The alkyl or alkenyl substituent $R_1$ imparts higher volatility, so that the organometallic compounds of this invention have lower boiling points and higher vapor pressures at 100° C. than do the analogous unsubstituted cyclopentadienyl compounds (those of the formula I above except that $R_1$ is hydrogen).

Representative organometallic precursor compounds of formula (I) which are suitable for depositing a transition metal include the following:

Group VB: bis(isopropylcyclopentadienyl) vanadium, tetra(isoproylcyclopentadienyl) tantalum; isopropylcyclopentadienyl tantalum dihydride.

Group VIB: bis(isopropylcyclopentadienyl) chromium and tetra(ispropylcyclopentadienyl) molybdenum; di(isopropylcyclopentadienyl) molybdenum dihydride, and di(isopropylcyclopentadienyl) tungsten dihydride.

Group VIIB: bis(isopropylcyclopentadienyl) manganese, isopropylcyclopropylcyclopentadienyl manganese hydride, and di(isopropylcyclopentadienyl) rhenium monohydride.

Group VIII: bis(isopropylcyclopentadienyl) iron, bis(isopropylcyclopentadienyl) cobalt, bis(isopropylcyclopentadienyl) ruthenium, bis(isopropylcyclopentadienyl) osmium, and bis(isopropylcyclopentadienyl) iridium; isopropylcyclopentadienyl nickel isopropyl, isopropylcyclopentadienyl nickel allyl.

Numerous organometallic compounds of formula (I) which are suitable as precursors have not been specifically named, in order to avoid an unduly lengthy list. Only isopropylcyclopentadienyl metal compounds have been named in most cases; the lower alkylcyclopentadienyl metal homologs and alkenylcyclopentadienyl metal analogs in which the substituent $R_1$ is any lower alkyl or alkenyl radical of 2 to 6 carbon atoms, are equally suitable. Similarly, not all possible hydrocarbyl radicals $R_2$ have been specifically named.

GENERAL METHOD FOR PREPARING PRECURSORS

Organometallic precursor compounds of Formula (I) can be prepared by the general method described below. This method proceeds according to the following equations (1) through (4)

$$C_5H_6 + Na \rightarrow NaC_5H_5 + \tfrac{1}{2}H_2 \qquad (1)$$

$$NaC_5H_5 + R_1Br \rightarrow R_1C_5H_5 + NaBr \qquad (2)$$

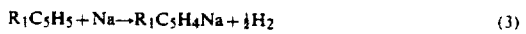
$$R_1C_5H_5 + Na \rightarrow R_1C_5H_4Na + \tfrac{1}{2}H_2 \qquad (3)$$

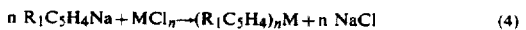
$$n\, R_1C_5H_4Na + MCl_n \rightarrow (R_1C_5H_4)_nM + n\, NaCl \qquad (4)$$

Sodium cyclopentadienide may be prepared according to equation (1) by reacting monomeric 1,3-cyclopentadiene in an inert solvent such as tetrahydrofuran (THF) with an excess of metallic sodium. The resulting solution of sodium cyclopentadienide (in THF) may be reacted in another vessel (away from excess sodium) with a lower alkyl or alkenyl bromide (e.g., isopropyl bromide or allyl bromide) according to equation (2) by adding the alkyl or alkenyl bromide through a dropping funnel. The resulting sodium bromide is allowed to settle. The alkyl- or alkenylcyclopentadiene in solution produced may be separated from the sodium bromide and the solvent (e.g. THF) by fractional distillation, and then reacted with a further quantity of metallic sodium (e.g., as fresh sodium beads) according to equation (3). This reaction may be carried out at a slightly elevated temperature (e.g., 40° C. overnight). The resulting solution of sodium alkylcyclopentadienide is reacted with a transition metal halide, (preferably in excess), producing an alkylcyclopentadienyl metal compound, which may be represented by formula (I). The entire series of reactions is carried out in the absence of air, e.g., under vacuum or in an argon atmosphere.

Precursors of formula (I) containing an $R_2$ group (i.e., compounds in which p is not zero) can be prepared by methods such as those illustrated in preparations B and C hereinafter.

DEPOSITION OF THIN COATINGS

It is possible to prepare thin coatings of alloys, pure metals, mixtures and compounds of transition metals according to this invention.

Pure metals are deposited by contacting an organometallic precursor compound of the formula (I) with a heated substrate under nonoxidizing and preferably reducing conditions.

Alloys, metal mixtures and intermetallic compounds can also be deposited in accordance with this invention, by contacting one or more precursor compounds of formula (I) and one or more additional heat decomposable precursor compounds which yield the desired additional metals or metalloids on decomposition, with a heated substrate under nonoxidizing and preferably reducing conditions. The additional precursor compounds are preferably organometallic compounds which meet the general requirements for precursors started earlier. By way of example, molybdenum disilicide, which is an intermetallic compound, can be deposited according to this invention by contacting a molybdenum compound of formula (I), such as tetra(isopropylcyclopentadienyl) molybdenum, and a silicon precursor compound, such as silane, with a heated substrate under nonoxidizing conditions. Molybdenum diselenide may be deposited similarly using a molybdenum precursor of formula (I) and a selenium precursor such as diethylselenide. The term, "metalloid", as used herein refers to a solid nometallic element other than sulfur or a halogen, and in particular refers to arsenic, antimony, boron, germanium, phosphorus, selenium, silicon and tellurium. Other terms used herein, such as "intermetallic compound" and "organometallic compound", are used in accordance with "The Condensed Chemical Dictionary" 10th edition, cited supra.

Metal oxide coatings can be formed by using as precursor a compound of formula (I) which yields the desired metal on decomposition. The precursor is contacted with a heated substrate in the presence of an oxidizing agent, which is a mildly oxidizing gaseous oxygen source. The oxidizing agent may be any gaseous reactant which is capable of reacting with the organometallic precursor compound(s) at the decomposition temperatures of the latter to form metal oxide deposits. Oxygen compounds, such as nitrous oxide, carbon dioxide, THF (tetrahydrofuran) and steam, are better suited than oxygen or air to the deposition of metal oxides and oxygen-containing salts because the oxygen compounds react with organometallic compounds only at high temperatures. The oxidizing agent may be introduced into the reactor in admixture with a carrier gas. For example, when a vanadium pentoxide coating is desired, the precursor may be tris(isopropylcyclopentadienyl) vanadium or other vanadium compound of formula (I). For example, nitrous oxide/nitrogen and carbon dioxide/hydrogen oxidizing mixtures are suitable.

The above method for preparing oxide coatings can be used with appropriate choice of precursors and oxidizing agent, to prepare other coatings (e.g., transition metal salts) containing a one or more transition metals of Groups VB to VIII, an oxidizing nonmetal (e.g., oxygen, sulfur or a halogen), and optionally one or more additional metals or metalloids (i.e., those not in Groups VB to VII). Examples of such coatings include lithium niobate, molybdenum disulfide, managanese antimonide, etc. In general these are salts of transition metals of Groups VB to VIII.

Appropriate precursors are one or more transition metal compounds of formula (I) and one or more organometallic compounds yielding the desired additional metals or metalloids. When the oxidizing nonmetal of the coating is other than oxygen (i.e., sulfur or a halogen), an appropriate oxidizing agent, e.g., a sulfite, or a sulfide plus oxygen or an oxygen compound, or a halogen (e.g., chlorine), or a combination of a hydrogen halide (e.g., HCl) plus oxygen or compound yielding oxygen, is chosen.

The substrate can be any material, usually either metallic or ceramic, on which an adherent metallic coating can be formed and which can be heated to a temperature above the decomposition temperatures of the precursor compounds. Thus, the substrate can be a ceramic material such as glass or quartz, or a metal such as iron, nickel, titanium, tungsten, copper or aluminum. The substrate must be a solid at the decomposition temperature of the precursor. This poses no problems when the melting or softening point of the substrate is above 1000° C. When the desired substrate has a melting or softening point below about 1000° C. (which is the case with aluminum, certain other metals, and most glasses), one must use a precursor compound whose decomposition temperature is lower than the melting or softening point of the desired substrate.

The substrate can be of any desired shape, either regular or irregular. Thus, the substrate can be a rectangular solid or other solid characterized by flat exterior surfaces. Cylindrical surfaces, such as rods and wires, can also be coated according to this invention. Spherical surfaces and other curved surfaces can also be coated. The substrate can even be hollow, as for example, a tube or a hollow sphere having openings to the exterior.

Ductile metallic rods and wires are preferred substrates.

The desired metallic coating can be formed on the desired substrate by methods known in the art. "Metallic" in this connection includes pure metals, mixtures, alloys, and metal compounds (including intermetallic compounds, metal oxides and salts). Conventional chemical vapor deposition (CVD), chemical beam epitaxy (CBE) or metal-organic molecular beam epitaxy (MO-MBE) techniques, and variations thereof, can be used. Broadly, "chemical vapor deposition" or "CVD" includes any process in which a metallic coating is deposited on a heated substrate by decomposition of one or more precursor compounds. In conventional CVD the reactants are carried into the deposition region by carrier gas flow. Where, as here, a metallic coating is to be formed on a heated substrate, it is usually desirable to convey the organometallic precursor compound(s) and the oxidizing agent (where used) to the substrate in separate carrier gas streams in order to avoid premature reaction. In CBE or MO-MBE (these two terms are used synonymously herein), the reactants are introduced as separate streams into a high vacuum chamber and expanded to form molecular beams which are impinged line of sight on to a heated substrate. The molecular beams strike the hot substrate and deposit metals, which may be oxidized by an oxidizing gas stream to the corresponding oxides. Conventional CVD, CBE and MO-MBE techniques have been described in the literature, particularly the literature pertaining to deposition of silicon and III-V and II-VI compounds.

The foregoing processes can be carried out in any apparatus which includes a gas-tight chamber or gas space having means for supporting a substrate, means for heating this substrate to a temperature above the decomposition temperature of the decomposable metal compound, an inlet conduit for admitting gas or vapor streams of decomposable organometallic compound and oxidizing agent, and an outlet conduit for removing a stream of carrier gas, decomposition products and undecomposed metal compound from the chamber. Suitable apparatus of various types are well known in the art.

For CVD processes it is preferred to supply the organometallic compound(s), and the oxidizing agent where used, in streams of carrier gas. The preferred carrier gas for the organometallic compound is hydrogen, argon, nitrogen, or a mixture of these. The desired mole fraction can be achieved by bubbling the carrier gas through a body or pool of the liquid organometallic compound at a rate and bubbler temperature (which is the same as the pool temperature) which will give the desired mole reaction. The bubbler temperature is typically from the melting point of the organometallic compound to about 150° C. When two or more precursor compounds are used, they are preferably entrained in separate carrier gas streams, which may be combined into a single carrier gas stream, prior to entry into the reactor, unless interaction between the precursors may result. It is possible to supply the organometallic compounds in undiluted form at reduced pressure (say about 0.1 atmosphere or less) to the reactor, but use of a carrier gas is generally preferred because it affords better process control and does not require as high a vacuum. The oxidizing agent (e.g., nitrous oxide, carbon dioxide, THF or steam) is also preferably contained in a non-oxidizing carrier gas. For example, nitrous oxide may be diluted with nitrogen, and carbon dioxide and steam can be diluted with hydrogen. Separate streams of organometallic compounds and oxidizing agent are supplied to avoid premature decomposition of the organometallic compounds.

The substrate temperature for all processes according to this invention, whether CVD, MO-MBE (metalorganic molecular beam epitaxy) or CBE (chemical beam epitaxy) is above the decomposition temperature of the organometallic precursor compound, and is in the range of about 150° C. to about 1000° C. A preferred substrate temperature is in the range of about 500°-600° C. regardless of which process is used.

CVD processes using a carrier gas are typically carried out in the pressure range of about 0.1 torr to about atmospheric pressure (760 torr), although higher or lower pressures can be used. MO-MBE or CBE process are typically carried out under high vacuum. For example, in preferred MO-MBE and CBE process, the reactor pressure is typically about $10^{-5}$ torr during crystal growth (i.e., while organometallic compounds are actually being supplied to the substrate), with a typical background pressure from $10^{-10}$ to $10^{-9}$ torr. The low background pressure in MO-MBE allows for fast switching of material composition, which is important in growing ultra thin layers and other multilayer coatings in which there are abrupt composition and sloping changes from layer to layer.

Decomposition products are removed from the reactor in all processes herein described via the outlet provided for that purpose.

Products of this invention may have any desired coating thickness ranging from monomolecular up to about one millimeter. A preferred range of thickness is from about 0.1 to about 100 microns, especially from about 0.1 to about 20 microns. Coating thickness can be controlled by controlling the flow rate of the organometallic compounds and the length of time over which these compounds are supplied. Products of this invention may be characterized as composite articles having a thin metallic coating thereon.

Single layer coatings, usually of substantially uniform composition throughout, can be achieved with any of the processes described herein. Multiple layer coatings having different compositions are best achieved with MO-MBE or CBE.

Epitaxial, polycrystalline and amorphous coatings can all be obtained in accordance with this invention.

Coatings produced according to this invention usually have a high degree of conformality. That is, the thickness of the coating is very nearly uniform even when the substrate has an irregular rough surface. This can be realized by depositing the coating in a surface kinetic limited regime (i.e., under conditions such that surface kinetics limit the deposition rate) at relatively low temperatures.

Processes of this invention offer a range of composite articles, comprising a metallic coating or film on a substrate, at low cost. High quality films of excellent purity are obtained. Low operating temperatures can be used, since in general the organometallic precursor compounds used herein have lower decomposition temperatures than their unsubstituted cyclopentadienyl metal analogs. Faster metal oxide deposition rates are made possible, particularly in CVD processes, by the relatively high vapor pressures of the organometallic precursor compounds used herein. The relatively wide "window" or temperature range between melting point and decomposition temperature makes the precursor compounds herein easy to handle.

Coatings may be deposited on conventional insulating substrates such as glass, plastic or printed circuit board. Desired patterns can be formed by conventional techniques. Products of this invention have a number of uses. The uses include ferroelectric devices, storage devices, dielectric amplifiers and magnetooptic devices. Other uses include rectifiers, thin film resistors and capacitors, infrared windows and optical elements, ferroelectric materials, long wavelength optical fibers, magnetic thin films for optics and storage, solar cells, phosphors for television tubes, decorative coatings, and optical mirrors and coatings.

Preparation of precursors will be described further with reference to the specific preparation method which follow. All precursor preparation methods, including those used to prepare precursors which are believed to be novel and patentable, will be headed "Preparation".

PREPARATION A

Bis(isopropylcyclopentatienyl)vanadium;

Sodium cyclopentadienide is prepared by using 30 g of fine sodium beads (a two fold excess) and 50 ml of monomeric cyclopentadiene in 500 ml of tetrahydrofuran (THF). This solution is then transferred to another vessel (away from excess sodium) and stirred while adding 60 ml of isopropyl bromide from a dropping funnel. After completion the NaBr is allowed to settle. The slightly yellow solution containing isopropylcyclopentadiene is then transferred to another vessel containing an excess of fresh sodium beads. The solution is heated to 40° C. and allowed to stir overnight to insure complete reaction. This solution containing sodium isopropylcyclopentadienide is transferred into another flask onto 50 g of anhydrous vanadium dichloride and allowed to stir at 60° C. for 3 hours. The excess $VCl_2$ and NaCl were allowed to settle. The solution containing bis(isopropylcyclopentadienyl) vanadium is transferred to another flask and solvent was removed by vacuum at or below room temperature. The product is removed by vacuum distillation at $10^{-2}$ torr in the temperature range of 180° C. to 195° C.

Other metal isopropylcyclopentadienyl compounds, e.g., those of niobium, tantalum, chromium, molybdenum, maganese, iron, cobalt, ruthemium, osmium and iridium, can be prepared according to Preparation A, substituting a halide of the desired metal for vanadium chloride.

Homologs and analogs, e.g., metal ethylcyclopentadienyl compounds, metal butylcyclopentadienyl compounds, metal allycyclopentadienyl compounds, etc., can be prepared according to Preparation A, substituting the appropriate alkyl or alkenyl halide, e.g., ethyl bromide, butyl bromide, allyl bromide, etc., for isopropyl bromide.

PREPARATION B

Di(Isopropylcyclopentadienyl) Molybdenum Dihydride

Sodium isopropylcyclopentadienide is prepared in THF as described in Preparation A. Then, anhydrous molybdenum pentachloride (0.1 mole) is slowly added to an ice-cooled solution of sodium isopropylcyclopentadienide (0.7 mole) in THF (150 ml) containing sodium borohydride (10 g). The mixture is stirred for four hours under reflux. After removal of the solvent in a vacuum the product is distilled from the residue at $10^{-2}$ torr in the range of 30°-40° C.

Other isopropylcyclopentadienyl metal hydrides, such as those of tungsten, tantalum and rhenium, can be prepared according to Preparation B, substituting a halide of the desire metal for molybdenum pentachloride.

Homologs and analogs, e.g., ethylcyclopentadienyl molybdenum hydride, butylcyclopentadienyl molybdenum hydride and allylcyclopentadienyl molybdenum hydride can be prepared according to Preparation B, substituting the appropriate alkyl or alkenyl halide, such as ethyl bromide, butyl bromide or allyl bromide for isopropyl bromide.

PREPARATION C

Isopropylcyclopentadienyl nickel allyl

Sodium isopropylcyclopentadienide is prepared in THF as described in Preparation A. Then dimeric allyl nickel bromide is prepared by reacting 70 g of nickel carbonyl and 50 ml of allyl bromide in 200 ml of THF. The final solution is added dropwise onto the solution of sodium isopropylcyclopentadienide and allowed to stir at room temperature for two hours. The mixture becomes violet immediately and NaBr precipitates. The solution containing isopropylcyclopentadienyl nickel allyl is transferred to another flask and solvent is removed by pumping at or below room temperature. The product is removed by vacuum distillation at $10^{-2}$ torr in the range of 30°-40° C.

Other metal analogs of the title compound, such as isopropylcyclopentadienyl palladium allyl and isopropylcyclopentadienyl platinum triisopropyl, can be made according to Preparation C, substituting the appropriate palladium or platinum compound for the corresponding nickel compound. Compounds of other metals, e.g., osmium and iridium, can be similarly prepared.

Homologs and analogs of the title compound such as ethylcyclopentadienyl nickel allyl, butylcyclopentadienyl nickel allyl and allylcyclopentadienyl nickel allyl, can be prepared according to Preparation C, substituting an appropriate alkyl or alkenyl halide such as ethyl bromide, butyl bromide or alkyl bromide, for isopropyl bromide.

Homologs and analogs of the title compound, such as isopropylcyclopentadienyl nickel methyl, isopropylcyclopentadienyl nickel ethyl and isopropylcyclopentadienyl nickel butyl, can be prepared according to Preparation C, substituting methyl bromide, ethyl bromide or, butyl bromide for allyl bromide.

This invention will now be further described with reference to the examples which follow.

EXAMPLE 1

Deposition of Vanadium Film by CVD

A gas-tight reactor having inlet and outlet ports and a quartz plate substrate mounted on a susceptor therein, is purged with a flowing stream of argon gas. The reactor is depressured to a pressure of 5 torr, and the substrate is heated by electrical resistance heating to a temperature of 600° C. A stream of purified argon carrier gas is bubbled through a pool of bis(isopropylcyclopentadienyl) vanadium, which is at a temperature of 140° C. The carrier gas flow rate is 500 sccm. The resulting gas stream is continuously flowed into the reactor through a heated line while the substrate temperature is maintained at 600° C. Carrier gas with some unreacted precursor therein is continuously withdrawn through the outlet port of the reactor. Gas flow is continued for one hour. A vanadium film about one micron thick is deposited. The reactor is then again purged with argon, repressured to atmospheric pressure with argon and then allowed to cool. The substrate with the vanadium film deposited thereon is removed from the reactor.

Other carrier gases, such as hydrogen, can be used in place of argon if desired. Use of hydrogen as the carrier gas would be expected to eliminate carbon incorporation, which is sometimes observed when argon is used as the carrier gas.

Thin films of other metals, such as niobium, tantalum, chromium, molybdenum, manganese, iron, cobalt, ruthenium, osmium and iridium, can be deposited according to Example 1, using the desired metal isopropylcyclopentadienyl in place of bis(isopropylcyclopentadienyl) vanadium.

EXAMPLE 2

Deposition of Mo film by CVD

The procedure of Example 1 is followed except that the precursor compound is isopropylcyclopentadienyl molybdenum hydride. A thin molybdenum film is deposited on the substrate.

Films of other metals, such as tungsten, manganese and rhenium can be deposited by using the isopropylcyclopentadienyl metal hydride according to Example 2.

EXAMPLE 3

Deposition of Ni film by CVD

The procedure of Example 1 is followed except that the precursor compound is isopropylcyclopentadienyl nickel isopropyl. A thin nickel film is deposited on the substrate.

Homologs and analogs of isopropylcyclopentadionyl nickel isopropyl, such as compounds of formula (I) in which $R_1$ is ethyl, butyl or allyl, and/or $R_2$ is methyl, ethyl, or allyl, can be used in place of isopropylcyclopentadienyl nickel isopropyl in the procedure of Example 3 with similar results.

EXAMPLE 4

Deposition of MoSi$_2$ film

The procedure of Example 1 is followed except that separate streams of bis(isopropylcyclopentadienyl) molybdenum hydride and silane, both in argon as the carrier gas, are flowed into the reactor at flow rates of 500 sccm and 100 sccm, respectively. Concentrations are such as to give mole fractions of about $1.5 \times 10^{-3}$ for Mo and $3 \times 10^{-3}$ for Si. Flow of precursors in carrier gas streams is continued for one hour. A thin film of molybdenum disilicide is deposited. After the flow of precursors has been stopped, the reactor is purged and repressured with argon, cooled and the coated substrate removed as in Example 1.

Other films of intermetallic compounds, such as molybdenum diselenide, can be deposited according to the procedure of Example 4 using appropriate precursors.

EXAMPLE 5

Deposition of V$_2$O$_5$ film by CVD

The procedure of Example 1 is followed, except that separate streams of bis(isopropylcyclopentadienyl)-vanadium in carrier gas (argon), and carbon dioxide/hydrogen mixture (oxidizing agent), are introduced into the reactor and directed towards the substrate. Mole fractions of vanadium precursor and carbon dioxide in the reactor are about $7.5 \times 10^{-4}$ and $10^{-2}$ respectively. A thin film of vanadium pentoxide is deposited at 500° C. The reactor is purged and the coated substrate removed as described in Example 1.

What is claimed is:

1. A chemical vapor deposition process for depositing a thin coating comprising a transition metal of Group VB, VIB, VIIB or VIII of the Periodic Table, or a compound thereof, on a heated substrate, which comprises: contacting a heat decomposable organometallic compound of the following formula (I)

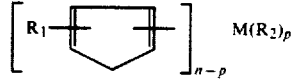

wherein:

M is a metal of Group VB, VIB, VIIB or VIII of the Periodic Table, $R_1$ is a lower alkyl or lower alkenyl radical of 2 to 6 carbon atoms, $R_2$ is hydrogen, a lower alkyl radical of 1 to about 6 carbon atoms, or a lower alkenyl radical of 2 to about 6 carbon atoms;

n is the valence of M and is an integer from 2 to 4, and p is an integer from 0 to $(n-1)$, with said heated substrate, the temperature of said substrate being above the decomposition temperatures of said organometallic compound.

2. A process according to claim 1 with the following provisos:

(1) M is a metal of Group VB, VIB, or VIII when $p=0$;

(2) M is a metal of Group VB, VIB or VIIB when $R_2$ is hydrogen; and (3) M is a Group VIIB or Group VIII metal when $R_2$ is a lower alkyl or lower alkenyl radical.

3. A process according to claim 1 in which M is a Group VB metal and (1) p is 0 or (2) $R_2$ is hydrogen and p is 1 or 2.

4. A process according to claim 1 in which M is a Group VIB metal and (1) p is 0 or (2) $R_2$ is hydrogen, and p is 1 or 2.

5. A process according to claim 1 in which M is a Group VIIB metal, $R_2$ is hydrogen and p is 1 or 2.

6. A process according to claim 1 in which M is a Group VIII metal and (1) p is 0 or (2) $R_2$ is a lower alkyl, or lower alkenyl radical and p is 1 or 2.

7. A process according to claim 1 in which $R_1$ is an alkyl radical, containing from 2 to about 4 carbon atoms.

8. A process according to claim 1 in which $R_1$ is isopropyl.

9. A process according to claim 1 in which said organometallic compound is supplied in a stream of non-oxidizing carrier gas.

10. A process according to claim 6 in which said substrate is in a non-oxidizing atmosphere.

11. A process according to claim 1 in which the temperature of said substrate is from about 150° to about 1000° C.

12. A process according to claim 1 in which said coating has a thickness not greater than about 100 microns.

13. An organometallic compound of the formula (I)

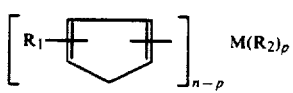

wherein:

M. is a metal of Group VB, VIB, VIIB or VIII of the Periodic Table;

$R_1$ is a lower alkyl or lower alkenyl radical of 2 to about 6 carbon atoms;

$R_2$ is hydrogen, a lower alkyl radical of 1 to about 6 carbon atoms, or a lower alkenyl radical of 2 to about 6 carbon atoms;

n is the valence of M and is an integer from 2 to 4, and p is from 1 to (n−1);

with the provisos that:
(1) M is a metal of Group VIB or VIIB when $R_2$ is hydrogen; and
(2) M is a metal of Group VIIB or VIII when $R_2$ is a lower alkyl, or lower alkenyl radical and p is from 1 to (n−1).

14. An organometallic compound according to claim 13 in which M is a Group VIB metal and $R_2$ is hydrogen.

15. An organometallic compound according to claim 13 in which M is a Group VIIB metal and $R_2$ is hydrogen or a lower alkyl, or lower alkenyl radical.

16. An organometallic compound according to claim 13 in which M is a Group VIII metal and $R_2$ is a lower alkyl or lower alkenyl radical.

17. An organometallic compound according to claim 16 in which M is a ferrous metal.

* * * * *

UNITED STATES PATENT AND TRADEMARK OFFICE
CERTIFICATE OF CORRECTION

PATENT NO. : 4,992,305
DATED : February 12, 1991
INVENTOR(S) : Ahmet Erbil

It is certified that error appears in the above-indentified patent and that said Letters Patent is hereby corrected as shown below:

On the title page, item [54] and col. 1, line 3:

That portion of the Title reading "TRANSISTION" should read --TRANSITION--.

Signed and Sealed this

Sixth Day of September, 1994

Attest:

BRUCE LEHMAN

Attesting Officer      Commissioner of Patents and Trademarks